United States Patent
Wang et al.

(10) Patent No.: US 6,262,142 B1
(45) Date of Patent: Jul. 17, 2001

(54) TRANSLUCENT WEAR RESISTANT DENTAL ENAMEL MATERIAL AND METHOD

(75) Inventors: Xiuling Wang, Milford, DE (US); John C. Subelka, Marlboro, NJ (US); Steven R. Jefferies, York, PA (US); Paul D. Hammesfahr, Wyoming; Paul A. Silver, Wilmington, both of DE (US)

(73) Assignee: DENTSPLY Research & Development, Milford, DE (US)

( * ) Notice: Subject to any disclaimer, the term of this patent is extended or adjusted under 35 U.S.C. 154(b) by 0 days.

(21) Appl. No.: 09/351,532

(22) Filed: Jul. 12, 1999

Related U.S. Application Data

(63) Continuation-in-part of application No. 09/136,320, filed on Jul. 6, 1998, which is a continuation-in-part of application No. 09/052,180, filed on Mar. 31, 1998, now abandoned, which is a continuation-in-part of application No. 08/946,612, filed on Oct. 7, 1997, now abandoned

(60) Provisional application No. 60/093,364, filed on Jul. 20, 1998, provisional application No. 60/043,812, filed on Apr. 14, 1997, and provisional application No. 60/042,585, filed on Apr. 2, 1997.

(51) Int. Cl.$^7$ .............. A61K 6/08; C08K 3/34; C08K 3/36

(52) U.S. Cl. .......... 523/116; 523/113; 523/115; 523/117; 524/700; 524/789

(58) Field of Search .................. 523/113, 115, 523/116, 117; 524/700, 789, 791

(56) References Cited

U.S. PATENT DOCUMENTS

| | | | |
|---|---|---|---|
| Re. 32,073 | 1/1986 | Randklev ............... | 523/117 |
| Re. 32,299 | 12/1986 | Radklev ................. | 501/59 |
| 4,107,845 | 8/1978 | Lee, Jr. et al. ......... | 523/116 |
| 4,115,346 | 9/1978 | Gross et al. ............ | 523/116 |
| 4,141,144 | 2/1979 | Lustgarten ............. | 523/113 |
| 4,226,622 | 10/1980 | Aliotta et al. .......... | 75/255 |
| 4,350,532 | 9/1982 | Randklev ............... | 523/117 |
| 4,358,549 | 11/1982 | Randklev ............... | 523/117 |
| 4,360,693 | 11/1982 | Orlowski ................ | 560/220 |
| 4,375,967 | 3/1983 | Schaefer ................. | 433/199 |
| 4,379,695 | 4/1983 | Orlowski et al. ...... | 433/217 |
| 4,381,918 | 5/1983 | Ehrnford ................ | 433/199 |
| 4,387,240 | 6/1983 | Berg ....................... | 556/440 |
| 4,392,828 | 7/1983 | Ehrnford ................ | 433/217 |
| 4,407,984 | 10/1983 | Ratcliffe et al. ........ | 523/115 |
| 4,490,115 | 12/1984 | Orlowski et al. ...... | 433/199 |
| 4,503,169 | 3/1985 | Randklev ............... | 523/117 |
| 4,514,174 | 4/1985 | Dougherty et al. .... | 433/226 |
| 4,514,342 | 4/1985 | Billington et al. ..... | 260/952 |
| 4,544,359 | 10/1985 | Waknine ................ | 523/115 |
| 4,547,531 | 10/1985 | Waknine ................ | 523/116 |
| 4,567,030 | 1/1986 | Yuasa et al. ........... | 423/326 |
| 4,636,533 | 1/1987 | Janda et al. ............ | 522/14 |
| 4,640,936 | 2/1987 | Janda et al. ............ | 522/14 |
| 4,649,165 | 3/1987 | Kuhlmann ............. | 523/116 |
| 4,656,053 | 4/1987 | Angrick et al. ........ | 427/53.1 |
| 4,658,558 | 4/1987 | Verble .................... | 52/410 |
| 4,758,612 | 7/1988 | Wilson et al. ......... | 524/5 |
| 4,814,362 | 3/1989 | Billington et al. ..... | 523/117 |
| 4,816,495 | 3/1989 | Blackwell et al. ..... | 522/14 |
| 4,978,007 | 12/1990 | Jacobs et al. .......... | 206/469 |

(List continued on next page.)

FOREIGN PATENT DOCUMENTS

| | | |
|---|---|---|
| 3416083 | 10/1985 | (DE) . |
| 195 24 362 | 1/1996 | (DE) . |
| 0053442 | 6/1982 | (EP) . |
| 0475239 | 9/1991 | (EP) . |
| 0222899 | 4/1992 | (EP) . |
| 0509516 | 10/1992 | (EP) . |
| 0530926 | 3/1993 | (EP) . |
| 0368657 | 8/1993 | (EP) . |
| 0434334 | 2/1994 | (EP) . |
| 0159887 | 7/1994 | (EP) . |
| 0 717 976 | 6/1996 | (EP) . |
| 0 832 636 | 4/1998 | (EP) . |
| 0839511 | 6/1998 | (EP) . |
| 63-199204 | 8/1988 | (JP) . |
| 8-140994 | 6/1996 | (JP) . |
| 92/08419 | 5/1992 | (WO) . |
| 93/12009 | 6/1993 | (WO) . |
| 96/03090 | 2/1996 | (WO) . |
| 98/432596 | 10/1998 | (WO) . |

OTHER PUBLICATIONS

Leinfelder et al in *An In Vitro Device for Predicting Clinical Wear*, Quintessence International, vol. 20, No. 10/1989, pp. 755–761.

Primary Examiner—Peter Szekely
(74) Attorney, Agent, or Firm—Dale R. Lovercheck; James B. Bieber

(57) ABSTRACT

A method and material for forming translucent wear resistant dental enamel and the dental enamel material formed which has an opacity less than 50 percent and a localized wear volume loss of less than 0.025 mm$^3$. The dental enamel material is formed from a polymerizable matrix and a filler. The material for forming translucent wear resistant dental enamel having an opacity less than 50 percent, a localized wear volume loss of less than 0.025 mm$^3$ and a localized extended wear volume loss of less than 0.04 mm$^3$, comprises a polymerizable matrix forming liquid and inorganic filler particles. The liquid comprises polymerizable material having a first refractive index. The filler comprising a first plurality of particles having a second refractive index. The first plurality of particles being formed from a low and a high median particle size plurality of particles. The low median particle size plurality of particles having a median particle size between 0.1 and 1.0 micrometers. The high median particle size plurality of particles having a median particle size between 1 and 10 micrometers. The first refractive index being within 5 percent of said second refractive index. More preferably the low median particle size plurality of particles have a median particle size between 0.3 and 0.7 micrometers, and said high median particle size plurality of particles have a median particle size between 1 and 2 micrometers. More preferably the filler further comprises a second plurality of filler particles having an average particle size of from about 0.01 to about 0.04 micrometers.

29 Claims, No Drawings

U.S. PATENT DOCUMENTS

| | | | |
|---|---|---|---|
| 5,009,597 | 4/1991 | Schaefer | 433/212.1 |
| 5,079,277 | 1/1992 | Wilson et al. | 523/116 |
| 5,089,051 | 2/1992 | Eppinger et al. | 106/35 |
| 5,106,304 | 4/1992 | Chronister | 433/228.1 |
| 5,172,809 | 12/1992 | Jacobs et al. | 206/368 |
| 5,218,070 | 6/1993 | Blackwell | 526/318 |
| 5,221,202 | 6/1993 | James | 433/9 |
| 5,228,907 | 7/1993 | Eppinger et al. | 106/35 |
| 5,252,697 | 10/1993 | Jacobs et al. | 528/60 |
| 5,295,827 | 3/1994 | Fundingsland | 433/80 |
| 5,338,773 | 8/1994 | Lu et al. | 523/116 |
| 5,348,154 | 9/1994 | Jacobs et al. | 206/369 |
| 5,350,059 | 9/1994 | Chester et al. | 206/63.5 |
| 5,350,782 | 9/1994 | Sasaki et al. | 523/116 |
| 5,354,785 | 10/1994 | Rheinberger et al. | 523/116 |
| 5,356,951 | 10/1994 | Yearn et al. | 523/116 |
| 5,377,823 | 1/1995 | Steen et al. | 206/63.5 |
| 5,378,737 | 1/1995 | Jacobs et al. | 523/116 |
| 5,418,262 | 5/1995 | Gobel | 523/116 |
| 5,425,640 | 6/1995 | Scharf | 433/215 |
| 5,538,129 | 7/1996 | Chester et al. | 206/63.5 |
| 5,547,379 | 8/1996 | Hasel | 433/212.1 |
| 5,548,001 | 8/1996 | Podszun et al. | 523/116 |
| 5,548,002 | 8/1996 | Schwabe et al. | 5823/118 |
| 5,609,675 | 3/1997 | Noritake et al. | 106/35 |
| 5,621,119 | 4/1997 | Podszun et al. | 549/229 |
| 5,708,051 | 1/1998 | Erdrich et al. | 523/116 |
| 5,710,194 | 1/1998 | Hammesfahr et al. | 523/116 |
| 5,749,730 | 5/1998 | Johnson et al. | 433/163 |
| 5,846,075 | 12/1998 | Suh et al. | 433/23 |
| 5,952,399 | 9/1999 | Rentsch | 523/116 |

TRANSLUCENT WEAR RESISTANT DENTAL ENAMEL MATERIAL AND METHOD

This is a continuation-in-part of provisional patent application Ser. No. 60/093,364 filed Jul. 20, 1998 which is a continuation-in-part of U.S. patent application Ser. No. 09/136,320, filed Jul. 6, 1998 which is a continuation-in-part of U.S. patent application Ser. No 09/052,180 filed Mar. 31, 1998 now abandoned, which is a continuation-in-part of patent application Ser. No. 08/946,612 filed Oct. 7, 1997 now abandoned, which have the benefit of the filing dates of provisional patent application No. 60/042,585 filed Apr. 2, 1997; and provisional patent application Ser. No. 60/043, 812 filed Apr. 14, 1997; each of which is incorporated herein by reference in its entirety.

The invention relates to a dental material useful in making artificial tooth enamel, inlays, onlays and veneers. The invention provides dental material preferably having an opacity less than 50 percent and a localized wear volume loss of less than 0.025 $mm^3$, formed from material having a hardenable matrix and a filler. A method according to the invention includes shaping the dental enamel material. Preferably the refractive index of the resin matrix material used to make artificial tooth enamel is within 5 percent of the refractive index of the filler material. More preferably, the refractive index of the resin matrix material is within 1 percent of the refractive index of the filler material. Most preferably, the refractive index of the resin matrix material is within 0.5 percent of the refractive index of the filler material.

The appearance of a dental restoration is modified not only by the intensity and shade of the pigments employed therein but also by the degree of translucency or opacity of the other material in the restorative. This is especially true of dental enamel.

BACKGROUND OF THE INVENTION

In the dental enamel art, translucency (the inverse of opacity) is a characteristic which is essential and improvements of 5 percent or more are widely recognized as being significant improvements in the art particularly when accompanied by acceptable wear resistance.

It is greatly preferred that dental enamel material be effectively homogeneous such that air bubbles or structural discontinuities are substantially avoided from introduction into the tooth structure. Additionally, it is preferred that such materials be capable of deforming a matrix band during the course of tooth filling. Such materials should also be capable of withstanding the physical stresses extant in the posterior region of the mouth and not crumble, fracture or erode under such conditions.

Opacity as used herein refers to the percentage of impinging white light transmitted from a spectrophotometer through a 1 mm thick sample of material being tested. More specifically, as used herein opacity of the sample of material, which is not pigmented, is measured using a Macbeth Color Eye Spectrophotometer calibrated according to the manufacturer's calibration method CAL-030-95, with the spectrophotometer connected to a CompuAid 286 microcomputer.

Localized wear volume loss (also known as volume loss of localized wear) as used herein refers to the volume loss in mm from a sample of material being tested after 250,000 cycles in a Leinfelder in vitro wear testing device as described in Leinfelder et al in *An In Vitro Device for Predicting Clinical Wear*, Quintessence International, Volume 20, Number 10/1989, pages 755–761. Measurements may be made for example using a VCA 2500 Video Contact Angle System, sold by AST Products, Inc., Billerica, Mass., and a microcomputer with MicroSoft Windows software, in accordance with the AST products User's Manual. The wear pistons are calibrated with the return limit set to 8.3 mm, load set to 10Kg Maximum, (the load applied to the piston being from 7.6 to 8.0 Kg), Crosshead speed set to 200 mm/min. Such device is in use at University of Alabama, University of North Carolina, Creighton University and at DENTSPLY International Inc.

Localized extended wear volume loss as used herein refers to the volume loss in $mm^3$ from a sample of material being tested after 400,000 cycles in a Leinfelder in vitro wear testing device as described in Leinfelder et al in *An In Vitro Device for Predicting Clinical Wear*, Quintessence International, Volume 20, Number 10/1989, pages 755–761. Measurements may be made for example using a VCA 2500 Video Contact Angle System, sold by AST Products, Inc., Billerica, Mass., and a microcomputer with MicroSoft Windows software, in accordance with the AST products User's Manual. The wear pistons are calibrated with the return limit set to 8.3 mm, load set to 10 Kg Maximum, (the load applied to the piston being from 7.6 to 8.0 Kg), Crosshead speed set to 200 mm/min. Such device is in use at University of Alabama, University of North Carolina, Creighton University and at DENTSPLY International Inc.

In measuring material volume loss the sample from the Leinfelder University of Alabama wear machine is measured for wear in the Form Taysurf profilometer which employs a transversing stylus to construct a 3D topographic map of the worn area by means of an electronic interface unit linked to a host computer. A surface analyzer program installed in the host computer graphically depicts the worn area and calculates its volume. This volume, expressed in cubic millimeters, is regarded as the "wear volume loss" of the material tested. The higher the volume loss, the greater the material wears.

The index of refraction (or refractive index) for any substance is the ratio of the velocity of light in a vacuum (Air at one atmospheric pressure is commonly used in place of a vacuum) to its velocity in the material being tested.

Liquid refractive index as used herein refers to the refractive index of a liquid. Preferably liquid refractive index as used herein is measured by a refractometer-Abbe Model (manufactured by BAUSH & LOMB).

Filler refractive index as used herein refers to the refractive index of inorganic filler particles. Preferably filler refractive index as used herein is that provided by the manufacturer, and may be measured, for example using a microscope.

Contrast ratio of dental composite is the ratio between the daylight apparent reflectance of the specimen when backed by a black standard and the reflectance of the specimen when backed by a white standard. The translucency of composite material is dependent on the particle size, shape and the difference in refractive indices between the glass filler and resin matrix in which the glass powders are located. The substantially perfect match (effective equality) in the refractive indices between inorganic glass filler and organic resin matrix used in the material of the invention results in the improved translucency of the dental enamel material of the invention.

Ethoxylated Bisphenol A Dimethacrylate (EBPADMA) also known as 2,2-Bis[4-(2-methacryloxyethoxy)phenyl] propane has the structural formula:

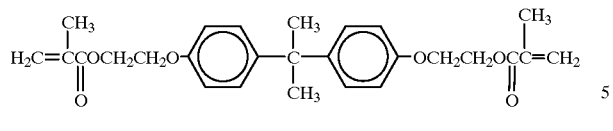

and is used as a resin matrix.

Triethylene glycol dimethacrylate also known as 2,2'[Ethanediylbis(oxy)bisethyl-di-2-methyl-propenate has the structural formula:

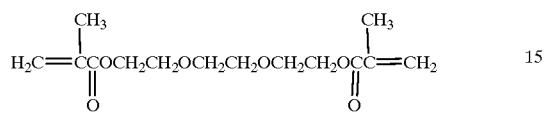

and is used as resin matrix.

Cyclodi-2,2'-bis{4-[3-methacryloxy-2-(1,12-dioxa-2,11-dioxo-3,10-diazadodecane)propoxy]phenyl} Propane (NCO Monomer) has the structural formula:

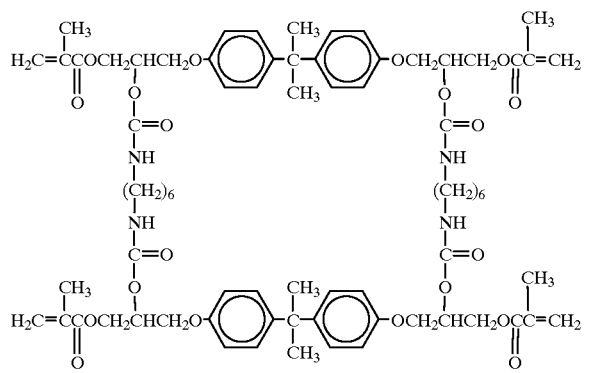

and is used as a resin matrix.

1,7,7,Trimethylbicyclo[2.2.1]heptane-2,3 dione (camphorquinone or CQ).

Ethyl-(4-N,N-dimethylamino)benzoate (EDAB) is a VLC initiating system and has a structural formula:

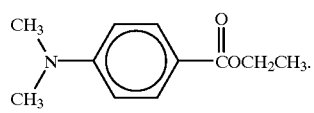

Butylated Hydroxy Toluene (BHT) also known as 2,6-bis(1,1-dimethylethyl)-4-methylphenol is a stabilizer having the structural formula:

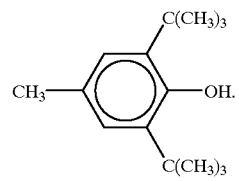

(2-Hydroxy-methoxyphenyl)phenyl Methanone is a UV stabilizer having the structural formula:

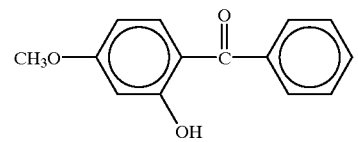

and sold by BASF Corporation as Uvinul M40.

Diethyl 2,5-dihydroxyterephthalate is a fluorescing agent having the structural formula:

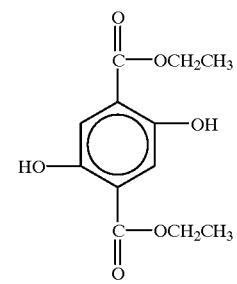

and is sold by Riedel-de Haën AG as Lumilux® Blau LZ.

2,7,7,9,15-Pentamethyl-4,13-dioxo-3,14-dioxa-5,12-diaza-hexadecane-1,16-diyldimethacrylate (UDMA) has a structural formula:

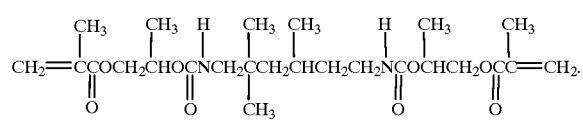

THE OBJECTS OF THE INVENTION

It is an object of the present invention to provide a dental enamel material having an opacity less than 50 percent and a localized wear volume loss of less than 0.025 mm$^3$.

It is a further object of the present invention to provide a polymerizable matrix forming liquid and inorganic filler particles, wherein the liquid comprises polymerizable material having a first refractive index, the filler comprises a plurality of particles having a second refractive index and having an average particle size of from about 0.1 to about 10 micrometers, and the first refractive index is within 5 percent of the second refractive index.

It is a further object of the present invention to provide such an enamel material, which is durable when, used in dental prosthetics.

These and other objects of the present invention which should become apparent from the description to follow, are carried out by the invention as hereinafter described and claimed.

SUMMARY OF THE INVENTION

A method and material for forming translucent wear resistant dental enamel and the dental enamel material formed which has an opacity less than 50 percent and a localized wear volume loss of less than 0.025 mm$^3$ and a localized extended wear volume loss of less than 0.04 mm$^3$. The dental enamel material is formed from a polymerizable matrix and a filler. The material for forming translucent wear resistant dental enamel having an opacity less than 50 percent and a localized wear volume loss after 250,000 cycles of less than 0.025 mm³, comprises a polymerizable matrix forming liquid and inorganic filler particles. The liquid comprises polymerizable material having a first refractive index. The filler comprising a first plurality of particles having a second refractive index. The first plurality of particles being formed from a low and a high median particle size plurality of particles. The low median particle size plurality of particles having a median particle size between 0.1 and 1.0 micrometers. The high median particle size plurality of particles having a median particle size between 1 and 10 micrometers. The first refractive index being within 5 percent of said second refractive index. More preferably the low median particle size plurality of particles have a median particle size between 0.3 and 0.7 micrometers, and said high median particle size plurality of particles have a median particle size between 1 and 2 micrometers. More preferably the filler further comprises a second plurality of filler particles having an average particle size of from about 0.01 to about 0.04 micrometers. Preferably the partcles of the second plurality of filler particles having an average particle size of from about 0.01 to about 0.04 micrometers are in agglomerated form having agglomerate sizes from about 0.2 micrometers to about 0.4 micrometers.

In accordance with a preferred embodiment of the invention is provided a material for forming translucent wear resistant dental enamel having an opacity less than 50 percent and a localized wear volume loss of less than 0.025 mm³, including a polymerizable matrix forming liquid and inorganic filler particles. The liquid comprises polymerizable material having a first refractive index. The filler comprises a first plurality of particles having a second refractive index and having an average particle size of from about 0.1 to about 10 micrometers. The first plurality of particles is formed from a low and a high median particle size plurality of particles. The low median particle size plurality of particles has a median particle size, preferably between 0.1 and 1.0 micrometers and more preferably between 0.3 and 0.7 micrometers. The high median particle size plurality of particles has a median particle size preferably between 1 and 10 micrometers and more preferably between 1 and 2 micrometers. The first refractive index is within 5 percent of said second refractive index. Preferably the filler comprises a plurality of filler particles having an average particle size of from about 0.01 to about 0.04 micrometers.

PREFERRED EMBODIMENTS FOR CARRYING OUT THE INVENTION

A dental enamel material according to the present invention includes a hardenable resin and filler. The enamel material can be put in place with respect to the dentition to be restored and then sculpted or carved as needed due to its non-flowing characteristics. The enamel material of the invention is useful as an enamel coating over restroative material in a tooth in a patient's mouth, as a veneer, as an inlay and as an onlay. The dental enamel material includes a polymeric matrix and a filler component. The filler comprises a first plurality of particles having a second refractive index and having an average particle size of from about 0.1 to about 10 micrometers. The first plurality of particles is formed, for example by blending two powders, one having a low and the other having a high median particle size plurality of particles. has a median particle size, preferably between 0.1 and 1.0 micrometers and more preferably between 0.3 and 0.7 micrometers. The high median particle size plurality of particles has a median particle size, preferably between 1 and 10 micrometers and more preferably between 1 and 2 micrometers. The first refractive index is within 5 percent of said second refractive index. Preferably the filler comprises a plurality of filler particles having an average particle size of from about 0.01 to about 0.04 micrometers.

One preferred filler material is a radiopaque dental glass. More preferably, the filler comprises a first plurality of preferably glass, more preferably barium glass, particles having an average particle size of from about 0.1 to about 10 and, a plurality of filler particles, preferably fumed silica, having an average particle size of from about 0.01 to about 0.04 micrometers. The inventive materials can be used as an intra-oral dental enamel, but can also be used by the laboratory technician in extra-oral dental applications such as in the production or restoration of crowns, inlays, and the like. The invention will be exemplified and discussed herein, for simplicity, with respect to intra-oral applications, it being understood that extra-oral applications are within the scope of the invention.

Examples of useful resins for compomers are those materials having as a principle functional ingredient, polymerizable unsaturated acidic monomers, such as a substituted butane moiety with acid or reactive acid derivative functionality. An example of an acid or reactive acid derivative functionality includes those having the general formula $(RO_2C)_x$—$C_4H_6$—$(CO_2R')_y$ where R is an acid radical or reactive acid derivative and R' is a polymerizable unsaturated radical having from about 2 to about 13 carbon atoms, x is 2 to 3 and y is 1 to 2. A description of such materials is provided in U.S. Pat. No. 5,218,070 which is herein incorporated by reference for such disclosure. A description of Examples of other useful resins is provided in U.S. Pat. No. 5,338,773 which is herein incorporated by reference for such disclosure.

Any hardenable resin matrix useful in intra-oral or extra-oral dental applications is within the scope of the invention. Preferred resins include those that are curable, more preferably curable by exposure to actinic light. Examples of such resins include ethoxylated bisphenol-A-dimethacrylate; Bisphenol-A-Glycidylmethacrylate; triethylene glycol dimethacrylate; and mixtures thereof. Optionally, a shading pigment or other additives may also be employed, such as for example, fluoride releasing agents, antibacterial agents, anticaries agents, and the like.

One preferred resin material is the reaction product of Bisphenol-A-Glycidylmethacrylate (Bis-GMA) and a chain initiator, such as hexamethylene diisocyanate (HMDI). The reaction may also include other reactive components. For example, the urethane component may be the reaction product of from about 27 to about 31 percent by weight of Bis-GMA as a reactive resin, more preferably about 29 percent by weight; from about 29 to about 33 percent by weight of triethylene glycol dimethacrylate (TEGDMA) as a reactive diluent, more preferably about 31 percent by weight; and, from about 29 to about 33 percent by weight of ethoxylated bisphenol-A-dimethacrylate (EBPADMA) also as a reactive diluent, more preferably about 31 percent by weight; with a useful amount of HMDI (preferably about 8 percent by weight). The reaction is preferably catalyzed with for example, a catalyst such as dibutyl tin dilaurate, and uses an inhibitor such as butylated hydroxy toluene.

Preferably, from about 97 to about 99 percent by weight of the urethane component, and more preferably about 98 percent by weight is used to form 100 percent by weight of the activated resin component. The remaining constituents of the activated resin include inhibitors, photoinitiators, UV absorbers, accelerators, fluorescing agents, and the like. While the preferred material is photocurable, a chemical cure package can also be used, including any of those well known in the art for dental use, including peroxide, amine, an ascorbic acid derivative, a metal ion salt, and the like.

Other useful resins can be employed including those disclosed in U.S. Pat. Nos. 4,514,342; 4,675,941; 4,816,495; 5,338,773 and 5,710,194 which are all herein incorporated by reference for such disclosure.

Examples of useful glass particles include barium aluminum-borosilicate glass, barium aluminofluorosilicate glass; mixtures thereof and the like. In these materials, barium can also be substituted by strontium and the like, and may also contain fluoride. Other useful materials include calcium hydroxyl ceramics, and others such as those fillers disclosed in U.S. Pat. Nos. 5,338,773; 5,710,194; 4,758,612; 5,079,277 and 4,814,362, all of which are herein incorporated by reference for such disclosure. These materials may have any morphology or shape, including spheres, regular or irregular shapes, filaments or whiskers, and the like. Any particle shape having the other characteristics of the invention as described herein, including for example, average particle size, is within the scope of the invention. Preferred such glasses are also silanated although this is not an absolute limitation of the invention. The filler particles may be silane treated (silane coupled) or provided with other treatments as is conventional for dental fillers.

In addition to opacity improvements, the materials according to the invention when compared to dental composite materials previously known exhibit similar or improved physical characteristics. For example, these include depth of cure, diametral tensile strength, transverse rupture strength, flexural modulus, radiopacity, hardness, fracture toughness, polymerization shrinkage and wear. These characteristics and their comparisons with known compositions will be more fully explored hereinbelow. It has also been found that the present materials can be polished to a high luster with conventional polishing techniques. It will be shown that certain characteristics, especially opacity and wear resistance are improved over the prior art materials.

It has been found that compositions according to the invention have good or even improved aesthetic characteristics. The materials are polishable to a high luster despite being highly filled. It has also been found that the products have excellent radiopacity approaching that of gold and amalgam products. It has further been found that the inventive materials have equal or superior post-cure or polymerization shrinkage characteristics as compared to conventional materials. It is to be appreciated that the inventive material shows similar or improved physical characteristics compared to the commercially available product. Most notably, the inventive material shows an improved translucency, and opacity.

EXAMPLE 1

A polymerizable monomeric resin matrix forming material having a refractive index of 1.52 was prepared by mixing at 23° C. 49.33 parts EBPADMA urethane resin mixture (reactive methacrylate resin); 49.33 parts NCO monomer mixture (reactive methacrylate resin); 0.025 parts butylated hydroxy toluene (BHT, inhibitor); 0.2 parts diethyl-2,5-dihydroxy-terepthalate (fluorescing agent); 1.0 parts (2-hydroxy-4-methoxyphenyl)phenyl methanone (UV stabilizer); 0.10 parts camphorquinone (photo initiator); and 0.04 parts ethyl-(4-N,N-dimethylamino)benzoate (accelerator).

EXAMPLE 1A

A polymerizable monomeric resin matrix forming material having a refractive index of 1.52 was prepared by mixing at 23° C. 97.8 grams EBPADMA urethane resin mixture (reactive methacrylate resin); 0.025 grams butylated hydroxy toluene (BHT, inhibitor); 0.2 grams diethyl-2,5-dihydroxy-terepthalate (fluorescing agent); 1.0 grams (2-hydroxy-4-methoxyphenyl)phenyl methanone (UV stabilizer); 0.165 grams camphorquinone (photo initiator); and 0.81 grams ethyl-(4-N,N-dimethylamino)benzoate (EDAB) (accelerator).

EXAMPLE 2

Filler blend was prepared by mixing barium fluoro alumino borosilicate glass (97 parts by weight) and silane treated fumed silica (TS720, 3.0 parts by weight). The barium fluoro alumino borosilicate glass has a refractive index of 1.52 and was first ground using ball-mill to an average diameter of 1.0 $\mu$m and then the glass was silanated. The filler comprises a first plurality of glass particles having an average particle size of from about 1 to about 10 micrometers; a second plurality of glass particles having an average particle size of from about 0.1 to about 1 micrometers. The fumed silica comprises a plurality of filler particles having an average particle size of from about 0.01 to about 0.04 micrometers.

EXAMPLE 3

Polymerizable composite forming composition was prepared by mixing 22.5 parts by weight of monomeric resin matrix (formed by following the procedure of Example 1) and 77.5 parts by weight of filler blend (prepared by following the procedure of Example 2). The polymerizable composition has the composition shown in Table 1. The composition is brushed onto an artificial tooth and polymerized to form a veneer composite having the physical properties shown in Table 1.

EXAMPLE 4

Polymerizable monomeric resin matrix forming material having a refractive index of 1.51 was prepared by mixing at 23° C. 49.31 parts EBPADMA urethane resin (reactive methacrylate resin); 19.74 parts NCO monomer (reactive methacrylate resin); 29.61 parts UDMA (reactive methacrylate resin); 0.025 parts butylated hydroxy toluene (BHT, inhibitor); 0.2 parts diethyl-2,5-dihydroxy-terepthalate (fluorescing agent); 1.0 parts (2-hydroxy-4-methoxyphenyl) phenyl methanone (UV stabilizer); 0.10 parts camphorquinone (photo initiator); and 0.04 parts ethyl-(4-N,N-dimethylamino)benzoate(accelerator).

EXAMPLE 5

Filler blend was prepared by mixing barium fluoro alumino borosilicate glass (99.5 parts by weight) and silane treated fumed silica (TS720, 0.5 parts by weight). The barium fluoro alumino borosilicate glass used has a refractive index of 1.52 and was first grounded using ball-mill to an average diameter of 1.0 $\mu$m and then the glass was silanated. The filler comprises a first plurality of glass particles having an average particle size of from about 1 to about 10 micrometers; a second plurality of glass particles having an average particle size of from about 0.1 to about 1 micrometers. The fumed silica comprises a plurality of filler particles having an average particle size of from about 0.01 to about 0.04 micrometers.

EXAMPLE 6

Polymerizable composite forming composition is prepared by mixing 23 parts by weight of the polymerizable monomeric resin matrix (prepared by following the procedure of Example 4) and 77 parts by weight of filler blend (prepared by following the procedure of Example 5). The polymerizable composition has the composition shown in Table 1. The composition is brushed onto an artificial tooth and polymerized to form a composite veneer having the physical properties shown in Table 1.

TABLE 1

FORMULATION AND PHYSICAL PROPERTIES

| | EXAMPLE | |
|---|---|---|
| | 3 | 6 |
| EBPADMA Urethane Resin | 11.10 | 11.34 |
| NCO Monomer | 11.10 | 4.54 |
| UDMA Resin | | 6.81 |
| BHT | 0.0058 | 0.0058 |
| Flublau Concentrate | 0.046 | 0.046 |
| Uvinul M40 | 0.23 | 0.23 |
| CQ | 0.023 | 0.023 |
| EDAB | 0.009 | 0.009 |
| Silanated Barium Alumino Fluorosilicate Glass (BAFG) | 75.18 | 76.61 |
| TS 720 | 2.32 | 0.39 |
| Compressive Strength (MPa) | 342.5 ± 54.4 | 392.8 ± 33.8 |
| Dimetral Tensile Strength (MPa) | 56.9 ± 6.3 | 56.2 ± 3.7 |
| Transverse Strength (MPa) | 143 ± 10 | 132 ± 21 |
| Flexural Modulus (GPa) | 9.6 ± 1.1 | 9.69 ± 0.62 |
| Barcol Hardness ("hard scale") | 77 | 72 |
| Depth of cure (mm) 20"/Spectrum | 13.2 | 9.94 |
| Water Sorption ($\mu$m/mm$^3$) | 13.443 | 14.545 |
| Shrinkage (%) | 3.5345 | 3.1825 |
| Fracture Toughness (Mpam$^{1/2}$) | 1.53 ± 0.30 | 1.42 ± 0.12 |
| Localized wear volume loss (mm$^3$) | 0.0123 | 0.0183 |
| Opacity (1 mm Thickness) | 45.92 | 36.03 |

Table 2 shows the localized wear volume loss from three commercial dental enamel products and the material formed in Example 3.

TABLE 2

| Product | Type | Manufacturer/Owner | Volume Lost (mm$^3$) | Opacity |
|---|---|---|---|---|
| Example 3 | Enamel | DENTSPLY | 0.012 | 39.86 |
| Example 6 | Enamel | DENTSPLY | 0.0183 | 36.03 |
| Licupast | Enamel | DeTech/DENTSPLY | 0.033 | 28.74 |
| Targis | Enamel | Ivoclar | 0.043 | — |
| Artglass | Enamel | Kulzer | 0.043 | 18.52 |
| Sculpture Super Clear | Enamel | Generic/Pentron | — | 30.83 |

Wear resistant low opacity dental enamel composite materials of the invention are formed from mixtures of polymerizable liquid and filler particles. The polymerizable liquid has a liquid refractive index and filler has a filler refractive index. Low opacity dental enamel composite materials of the invention are formed from mixtures of polymerizable liquid having a liquid refractive index and filler particles having a filler refractive index which is about the same as the liquid refractive index. In order of increasing preference the filler refractive index is within 5 percent, 4 percent, 3 percent, 2 percent, 1 percent or 0.5 percent of the liquid refractive index. In accordance with a preferred embodiment of the invention at least 70 percent of the filler has a refractive index which is within, in order of increasing preference, 5 percent, 4 percent, 3 percent, 2 percent, 1 percent or 0.5 percent of the liquid refractive index. Preferably at least 80 percent of the filler has a refractive index which is within, in order of increasing preference, 5 percent, 4 percent, 3 percent, 2 percent, 1 percent or 0.5 percent of the liquid refractive index. More preferably at least 90 percent of the filler has a refractive index which is within, in order of increasing preference, 5 percent, 4 percent, 3 percent, 2 percent, 1 percent or 0.5 percent of the liquid refractive index. Most preferably at least 99 percent of the filler has a refractive index which is within, in order of increasing preference, 5 percent, 4 percent, 3 percent, 2 percent, 1 percent or 0.5 percent of the liquid refractive index.

Preferably a material for forming translucent wear resistant dental enamel having an opacity less than 46 percent and a localized wear volume loss less than 0.025 mm$^3$, comprising: a polymerizable matrix forming liquid and inorganic filler particles, the liquid comprising polymerizable material having a first refractive index, the filler comprising a first plurality of particles having a second refractive index and having an average particle size of from about 0.1 to about 10 micrometers and a second plurality of filler particles having an average particle size of from about 0.01 to about 0.04 micrometers, and the first refractive index being within 5 percent of the second refractive index.

Preferably the material comprises from about 12 to about 25 percent by weight of the polymerizable matrix forming liquid and from about 75 to about 88 percent by weight of the filler. Preferably the polymerizable matrix forming liquid comprises polymerizable unsaturated acidic monomers of a substituted butane moiety with an acid or reactive acid derivative functionality.

Preferably the polymerizable matrix forming liquid comprises a photocurable resin. Preferably the opacity less than 46 percent and a localized wear volume loss less than 0.025 mm$^3$. Preferably the first refractive index is within 3% of the second refractive index. Preferably the first plurality of filler particles comprises glass selected from the group consisting of barium aluminum-borosilicate; barium aluminofluorosilicate; strontium aluminum-borosilicate; strontium aluminofluorosilicate.

Preferably the second plurality of particles comprises fumed silica. Preferably the filler comprises from about 60 to about 90 of barium glass particles; and, from about 10 to about 30 of fumed silica particles. Preferably the first refractive index is within 1 percent of the second refractive index. Preferably the second plurality of particles comprise less than 20 percent by weight of the filler and the first plurality of particles comprise more than 50 percent by weight of the filler. Preferably the second plurality of particles comprise less than 10 percent by weight of the filler and the first plurality of particles comprise more than 70 percent by weight of the filler.

The invention provides a method of forming translucent wear resistant dental enamel, comprising the steps of shaping polymerizable material to form tooth enamel; and, curing the polymerizable material; the polymerizable material comprising a polymerizable matrix forming liquid comprising polymerizable liquid having a first refractive index and filler particles; the filler comprising a first plurality of particles having a second refractive index and an average particle size of from about 0.1 to about 10 micrometers and a plurality of filler particles having an average particle size of from about 0.01 to about 0.04 micrometers, the first refractive index being within 1 percent of the second refractive index.

Preferably the invention provides a transparent wear resistant material having an opacity less than 46 percent and a localized wear volume loss less than 0.025 mm$^3$, formed by the process comprising: providing a mixture comprising a polymerizable matrix forming liquid and filler particles; and curing the liquid to form a dental enamel having an opacity of less than 50 percent and a localized wear volume loss of less than 0.025 mm$^3$. More preferably the invention provides dental enamel material having an opacity less than 46 percent and a localized wear volume loss less than 0.020 mm$^3$, formed from material having a hardenable matrix and a filler which includes fillers having two different particle sizes. Most preferably transparent wear resistant material in accordance with the invention has an opacity less than 40 percent and a localized wear volume loss less than 0.019 mm$^3$.

Preferably the liquid comprises polymerizable material having a first refractive index. Preferably the filler comprises a first plurality of particles having a second refractive index and an average particle size of from about 0.1 to about 10 micrometers and second plurality of filler particles having an average particle size of from about 0.01 to about 0.04 micrometers. Preferably the first refractive index is within 3 percent of the second refractive index. More preferably the first refractive index is within 1 percent of the second refractive index. Most preferably the first refractive index is within 0.5 percent of the second refractive index.

In accordance with a preferred embodiment of the invention is provided a material for forming translucent wear resistant dental enamel having an opacity less than 50 percent and a localized wear volume loss less than 0.025 mm$^3$, including a polymerizable matrix forming liquid and inorganic filler particles, The liquid comprising polymerizable material having a first refractive index. The filler comprising a first plurality of particles having a second refractive index and has an average particle size of from about 0.1 to about 10 micrometers. The first plurality of particles is formed from a low and a high median particle size plurality of particles. The low median particle size plurality of particles has a median particle size between 0.3 and 0.7 micrometers. The high median particle size plurality of particles has a median particle size between 1 and 2 micrometers. The first refractive index is within 5 percent of said second refractive index. Preferably, the material low median particle size plurality of particles comprises at least 40 percent by weight of the first plurality of particles. Preferably, the high median particle size plurality of particles comprises at least 40 percent by weight of the first plurality of particles. Preferably, the filler comprises more than 70 percent by weight of the material. Preferably, at least 90 percent by weight of the filler has a refractive index within 4 percent of the liquid refractive index and the filler further comprises a second plurality of filler particles having an average particle size of from about 0.01 to about 0.04 micrometers. Preferably, the liquid is cured to form polymeric material having a polymeric refractive index and at least 90 percent by weight of the filler has a refractive index within 2 percent of the polymeric refractive index. Preferably, at least 90 percent by weight of the filler has a refractive index within 1 percent of the liquid refractive index.

In each of Examples 7–9, 19.5 grams of the polymerizable monomeric resin matrix forming material formed by following the procedure of Example 1A is mixed with 80.5 grams of fillers to form polymerizable composite forming material. Table 3 shows the percent by weight of the fillers of Examples 7–9: course barium fluoride glass (mean particle size of 3.158 μm) and fine barium fluoride glass (average particle size of about 0.9 micron), 0×50 glass and in Examples 8 and 9, Cab-O-Sil TS720 glass. 0×50 glass is fumed SiO$_2$, average particle size 0.04 microns sold by DeGussa. Cab-O-Sil TS 720 glass is fumed SiO$_2$, average particle size 0.01 microns sold by CABOT. In each of Examples 7–9, the polymerizable composite forming material is brushed onto a natural tooth in a patient's mouth to form a polymerizable dentin layer, which polymerizes upon curing by exposure for 10 seconds to light from a MaxLite light curing unit sold by DENTSPLY to form a polymeric dentin layer. Polymerizable composite forming composition prepared by following the procedure of Example 3 is brushed onto the polymeric dentin layer and cured by exposure to the light for 10 seconds to form a polymeric enamel layer.

TABLE 3

| Example | Filler Fractions: Wt. Coarse BAFG: Fine BAFG:OX 50 + Other | Filler % wt/wt | Avg. Contrast Ratio/Opacity (3-1X30 mm discs) | 24 Hr. Traverse Strength - MPA | 24 Hr. Flexural Modulus - MPA | Polymerization Shrinkage - % | Localized Extended Wear Vol. Loss - mm | Packability Index - G/mm$^2$ |
|---|---|---|---|---|---|---|---|---|
| 7 | 20%:75%:5% | 80.5% | 45.03 | 147 | 10,770 | 2.29 | 0.038 | 714 |
| 8 | 20%:73%:5% + 2% TS-720 | 80.5% | 44.44 | 122 | 10,252 | 2.39 | 0.022 | 707 |
| 9 | 20% 73% 2% + 5% TS-720 | 80.5% | 43.80 | 112 | 10,799 | 2.29 | 0.034 | 683 |

EXAMPLE 10

23.0 grams of the polymerizable monomeric resin matrix forming material formed by the following the procedure of Example 1 is mixed with 77.0 gram of filler blend to form polymerizable composite forming material. The filler blend is formed by mixing 77.0 parts of fine milled barium fluoride glass, 20.0 parts of polymer coated silica (formed by following the procedure of Example 10A) and 3.0 parts Cab-O-Sil TS 720 fumed silica. 30 grams of polymerizable composite forming material is brushed onto a dental tooth in a patient's mouth and cured for 40 second of exposure to light from a Spectrum curing sold by DENTSPLY to form polymeric dentin layer of the tooth.

EXAMPLE 10A 63.54 parts SiO$_2$ particles having average particle size of 0.04 microns, 22.22 parts bis-GMA, 13.65 parts TEGDMA monomers and 0.55 parts initiator are mixed together. Then the mixture is heated to form polymer containing silica. The polymer containing silica is gound to form polymer coated SiO$_2$ particle having an average particle size of 20 microns.

EXAMPLE 11

Polymerizable composite forming composition was prepared by following the procedure of Example 3 is brushed onto the polymeric dentin layer of the tooth prepared by following the procedure of Example 10 and cured for 10 minutes of exposure to light from a Spectrum curing sold by DENTSPLY to form a veneer composite having the physical properties shown in Table 1 for Example 3.

EXAMPLE 12

23.0 grams of the polymerizable monomeric resin matrix forming material formed by the following the procedure of Example 1 is mixed with 77.0 gram of filler blend to form polymerizable composite forming material. The filler blend is formed by mixing 77.0 parts of fine milled barium fluoride glass, 20.0 parts of polymer coated silica (formed by following the procedure of Example 10A) and 3.0 parts Cab-O-Sil TS 720 fumed silica. 30 grams of polymerizable composite forming material is brushed onto a shaped gold dental alloy substrate supported by a tooth model and cured for 40 second of exposure to light from a Spectrum curing sold by DENTSPLY to form polymeric dentin layer of an indirect restoration.

EXAMPLE 13

Polymerizable composite forming composition was prepared by following the procedure of Example 3 is brushed onto the polymeric dentin layer of an indirect restoration prepared prepared by following the procedure of Example 12 and cured for 10 minutes of exposure to light from a Spectrum curing sold by DENTSPLY to form an indirect restoration having polymeric dentin layer and an enamel layer having the physical properties shown in Table 1 for Example 3.

The foregoing description illustrates preferred embodiments of the invention. However, concepts employed may, based upon the description, be used in other embodiments without departing from the spirit and scope of the invention.

What is claimed is:

1. A material for forming translucent wear resistant dental enamel having an opacity less than 50 percent and a localized wear volume loss of less than 0.025 mm$^3$, comprising:

a polymerizable matrix forming liquid and inorganic filler particles, said liquid comprising polymerizable material having a first refractive index, said filler comprising a first plurality of particles having a second refractive index, said first plurality of particles being formed from a low median particle size first plurality of particles, and a high median particle size second plurality of particles, said low median particle size plurality of particles having a median particle size between 0.3 and 0.7 micrometers, said high median particle size plurality of particles having a median particle size between 1 and 10 micrometers, and said first refractive index being within 5 percent of said second refractive index.

2. The material of claim 1 wherein said high median particle size plurality of particles have a median particle size between 1 and 2 micrometers.

3. The material of claim 1 wherein said filler further comprises a second plurality of filler particles having an average particle size of from about 0.01 to about 0.04 micrometers.

4. The material of claim 1 wherein at least 90 percent by weight of said filler has a refractive index within 4 percent of the liquid refractive index and said filler further comprises a second plurality of filler particles having an average particle size of from about 0.01 to about 0.04 micrometers.

5. The material of claim 1 wherein at least 90 percent by weight of the filler has a refractive index within 2 percent, of the liquid refractive index.

6. The material of claim 1 wherein at least 90 percent by weight of the filler has a refractive index within 1 percent of the liquid refractive index.

7. The material of claim 1 wherein at least 90 percent by weight of the filler has a refractive index within 0.5 percent of the liquid refractive index, and said translucent wear resistant dental enamel has an opacity less than 46 percent and a localized wear volume loss less than 0.022 mm$^3$.

8. The material of claim 1 wherein at least 99 percent by weight of said filler has a refractive index within 4 percent of the liquid refractive index.

9. The material of claim 1 wherein at least 99 percent by weight of said filler has a refractive index within 2 percent of the liquid refractive index.

10. The material of claim 1 wherein at least 99 percent by weight of said filler has a refractive index which is within 0.5 percent of the liquid refractive index.

11. The material of claim 1, wherein said polymerizable matrix forming liquid comprises from about 12 to about 25 percent by weight of said material and said filler comprises from about 75 to about 88 percent by weight of said material.

12. The material of claim 1, wherein said polymerizable matrix forming liquid comprises polymerizable unsaturated acidic monomers of a substituted butane moiety with an acid or reactive acid derivative functionality.

13. The material of claim 1, wherein said polymerizable matrix forming liquid comprises a photocurable resin.

14. The material of claim 1, wherein said opacity less than 40 percent and a localized wear volume loss less than 0.022 mm$^3$.

15. The material of claim 1, wherein said first refractive index is within 3 percent of said second refractive index.

16. The material of claim 1 wherein said first plurality of filler particles comprises glass selected from the group consisting of barium aluminum-borosilicate; barium aluminofluorosilicate; strontium aluminum-borosilicate; strontium aluminofluorosilicate.

17. The material of claim 1, wherein said second plurality of particles comprises fumed silica.

18. The material of claim 1, wherein said filler comprises from about 60 to about 90 percent by weight of barium glass particles; and, from about 10 to about 30 percent by weight of fumed silica particles.

19. The material of claim 1, wherein said first refractive index is within 1 percent of said second refractive index.

20. The material of claim 1, wherein said second plurality of particles comprise less than 20 percent by weight of said filler and said first plurality of particles comprise more than 50 percent by weight of said filler.

21. The material of claim 1, wherein said second plurality of particles comprise less than 10 percent by weight of said filler and said first plurality of particles comprise more than 70 percent by weight of said filler.

22. A material for forming translucent wear resistant dental enamel having an opacity less than 50 percent and a localized wear volume loss of less than 0.025 mm$^3$, comprising:

a polymerizable matrix forming liquid and inorganic filler particles, said liquid comprising polymerizable material having a first refractive index, said filler comprising a first plurality of particles having a second refractive index and having an average particle size of from about 0.1 to about 10 micrometers, said first plurality of particles being formed from a low and a high median plurality of particles, said low median plurality of particles having a medium particle size between 0.3 and 0.7 micrometers, said high median plurality of particles having a median particle size between 1 and 2 micrometers, and said first refractive index being within 5 percent of said second refractive index.

23. The material of claim 22 wherein said low median plurality of particles comprises at least 40 percent by weight of said first plurality of particles.

24. The material of claim 22 wherein said high median plurality of particles comprises at least 40 percent by weight of said first plurality of particles.

25. The material of claim 22 wherein said filler comprises more than 70 percent by weight of said material.

26. The material of claim 22 wherein at least 90 percent by weight of said filler has a refractive index within 4 percent of the liquid refractive index and said filler further comprises a second plurality of filler particles having an average particle size of from about 0.01 to about 0.04 micrometers.

27. The material of claim 22 wherein said liquid is cured to form polymeric material having a polymeric refractive index and at least 90 percent by weight of the filler has a refractive index within 2 percent, of said polymeric refractive index.

28. The material of claim 22 wherein at least 90 percent by weight of the filler has a refractive index within 1 percent of the liquid refractive index.

29. A transparent wear resistant dental enamel material having an opacity less than 46 percent and a localized wear volume loss of less than 0.025 mm$^3$, comprising a polymeric matrix and at least 70 percent by weight inorganic filler, said filler comprising a low and a high median plurality of particles, said low median plurality of particles having a medium particle size between 0.3 and 0.7 micrometers, said high median plurality of particles having a median particle size between 1 and 2 micrometers.

* * * * *